United States Patent
Mueller et al.

(10) Patent No.: US 8,092,424 B2
(45) Date of Patent: Jan. 10, 2012

(54) SAFETY SYRINGE

(76) Inventors: Jeffrey T. Mueller, Scottsdale, AZ (US); Karl A. Poterack, Fountain Hills, AZ (US)

(*) Notice: Subject to any disclaimer, the term of this patent is extended or adjusted under 35 U.S.C. 154(b) by 127 days.

(21) Appl. No.: 12/563,343

(22) Filed: Sep. 21, 2009

(65) Prior Publication Data
US 2011/0071476 A1    Mar. 24, 2011

(51) Int. Cl.
*A61M 5/00*    (2006.01)

(52) U.S. Cl. .............. 604/110; 604/170.01; 604/187; 604/188; 604/192; 604/220; 604/240

(58) Field of Classification Search .............. 604/110, 604/158, 159, 160, 164.01, 164.04, 164.06, 604/170.01, 170.02, 181, 187, 188, 220, 604/227, 232, 240, 241, 242, 192, 243
See application file for complete search history.

(56) References Cited

U.S. PATENT DOCUMENTS

| | | |
|---|---|---|
| 1,087,845 A | 2/1914 | Stevens |
| 1,527,291 A | 2/1925 | Zorraquin |
| 1,867,624 A | 7/1932 | Hoffman |
| 2,623,521 A | 12/1952 | Shaw |
| 3,727,613 A | 4/1973 | Sorenson et al. |
| 4,425,120 A | 1/1984 | Sampson et al. |
| 4,627,841 A | 12/1986 | Dorr |
| 4,631,057 A | 12/1986 | Mitchell |
| 4,722,344 A | 2/1988 | Cambron et al. |
| 4,828,547 A | 5/1989 | Sahi et al. |
| 4,917,671 A | 4/1990 | Chang |
| 5,009,642 A | 4/1991 | Sahi |
| 5,292,310 A | 3/1994 | Yoon |
| 5,514,100 A | 5/1996 | Mahurkar |
| 5,578,053 A | 11/1996 | Yoon |
| 5,637,096 A | 6/1997 | Yoon |
| 5,743,882 A | 4/1998 | Luther |
| 5,951,520 A | 9/1999 | Burzynski et al. |
| 6,629,956 B1 | 10/2003 | Polidoro et al. |

*Primary Examiner* — Bhisma Mehta
(74) *Attorney, Agent, or Firm* — John D. Titus

(57) ABSTRACT

A safety syringe adapted consists of an outer casing that supports a conventional hypodermic needle and an inner casing which supports a blunt cannula that is disposed inside the inner lumen of the hypodermic needle. The inner casing is keyed to the outer casing by one or more pins that engage helical tracks formed along the inner surface of the outer casing. Rotation of the inner casing relative to the outer casing advances the inner casing so that the blunt cannula is moved from a retracted position within the needle to an extended position in which the blunt end of the cannula extends beyond the tip of the needle.

15 Claims, 4 Drawing Sheets

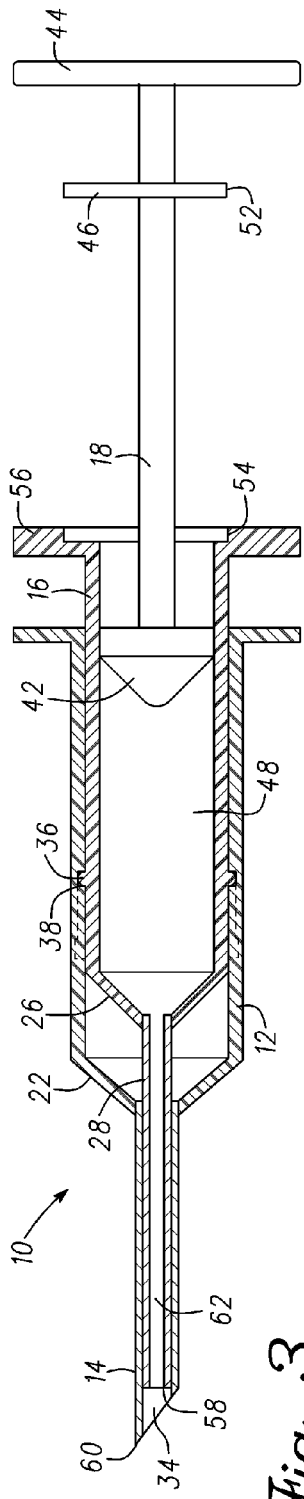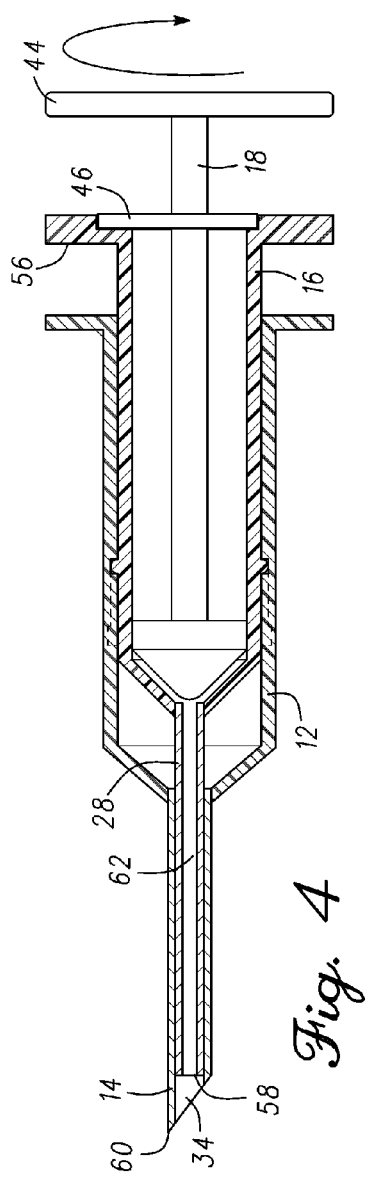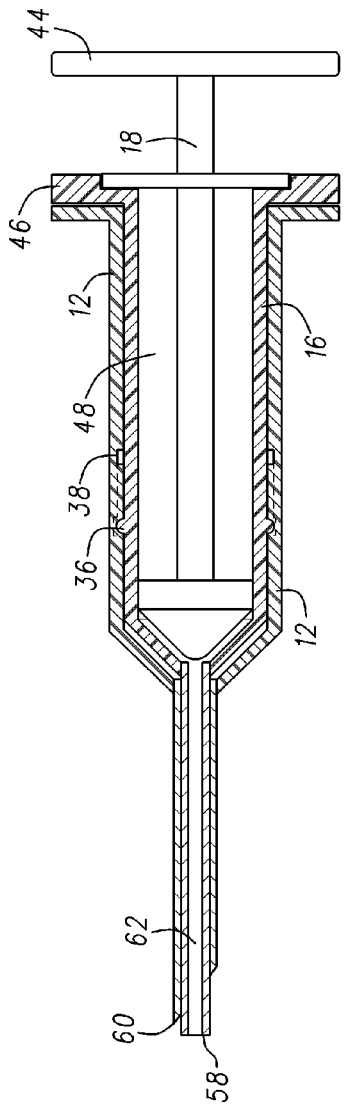

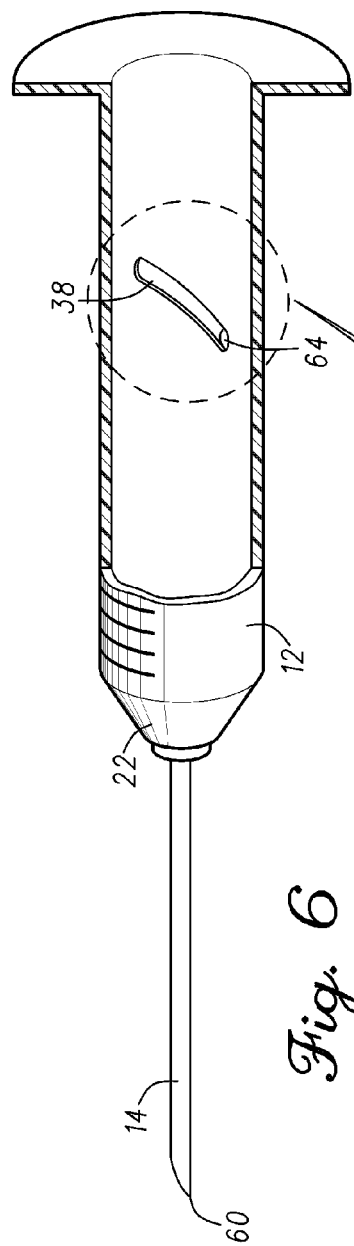
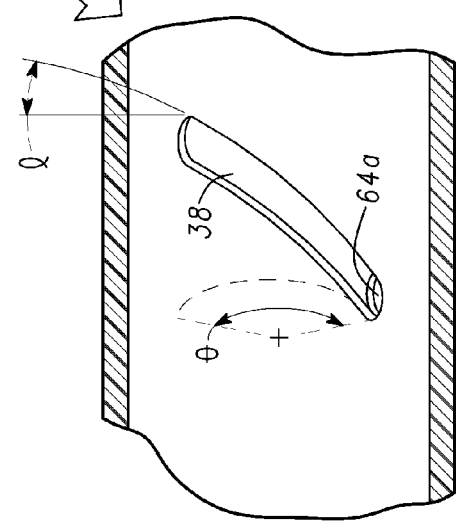
Fig. 6
Fig. 7
Fig. 8

SAFETY SYRINGE

BACKGROUND OF THE INVENTION

The present invention relates generally to medical equipment and more particularly to hypodermic syringes.

As is well known, hypodermic syringes are used in the medical and veterinary fields to inject substances into humans and animals. One problem presented by the use of hypodermic syringes is protecting those working with the syringes from accidental needle-stick wounds. This is particularly important with a hypodermic syringe that has been used because, following the injection, the needle may be contaminated and spread infections such as hepatitis and HIV.

Numerous efforts have been undertaken to provide means for shielding the sharp tip of the needle of a hypodermic syringe before and after use. One category of needle shields comprises a sheath that surrounds the external surface of the needle after use. One example of a sheath type device is disclosed in U.S. Pat. No. 4,631,057 to Mitchell. The shielded needle of Mitchell comprises a syringe having an external needle guard mounted to the body of the syringe. The needle guard is placed in a retracted position to expose the needle for use, then slid forward to an extended position over the sharp end of the needle after use. U.S. Pat. No. 4,425,120 to Sampson et al. also discloses a needle guard comprising a sheath that surrounds the body of the syringe that is advanced to cover the needle after use. A common disadvantage of sheath-type safety needles is that the sheath typically covers all or substantially all of the body of the syringe and, therefore, the body of the syringe cannot be manipulated directly by the medical professional when inserting the needle. Consequently, there is substantial "play" between the surface being held by the medical professional and the needle, which makes needle insertion more difficult to control.

A second broad category of safety needles comprise the so-called "stylet-type" safety needles in which a blunting stylet or cannula is advanced through the inner lumen of the needle. U.S. Pat. No. 1,087,845 to Stevens discloses a needle in which an inner blunt cannula is extended within the inner lumen of a sharp needle by means of a thumbscrew operating a miniature rack and pinion. U.S. Pat. No. 1,527,291 to Zorraquin discloses a needle with a blunt probe that is spring loaded into its extended position. The blunt tip springs forward when the needle has passed through the wall or membrane being penetrated, thereby giving the surgeon an indication when the needle has passed through the membrane. U.S. Pat. No. 1,867,624 to Hoffman discloses a biopsy needle consisting of an inner and outer cannula. U.S. Pat. No. 2,623,521 to Shaw discloses an indicating stylet needle with a blunt probe that is spring loaded into its extended position in a manner similar to Hoffman. U.S. Pat. No. 5,009,642 to Sahi et al. discloses a syringe in which the blunting stylet is spring-loaded and snaps forward into the extended position automatically when the plunger is fully depressed. All of the above patents have relatively complex and expensive mechanisms and, in the case of the spring-loaded stylets, present the possibility of accidental deployment of the blunting stylet when trying to withdraw medicine from an ampoule. What is needed, therefore, is a safety syringe that is free from the risk of accidental self-deployment that is simple to operate and inexpensive to manufacture.

BRIEF DESCRIPTION OF THE DRAWING

The present invention will be better understood from a reading of the following detailed description, taken in conjunction with the accompanying drawing figures in which like references designate like elements and, in which:

FIG. 3 is a cross-sectional view of the safety needle of FIG. 1 shown with the syringe plunger withdrawn;

FIG. 4 is a cross-sectional view of the safety needle of FIG. 1 shown with the syringe plunger fully depressed;

FIG. 5 is a cross-sectional view of the safety needle of FIG. 1 shown with the blunting cannula advanced;

FIG. 6 is a partial cross-sectional view of a needle carrier incorporating features of the present invention;

FIG. 7 is an enlarged view of a portion of FIG. 6;

FIG. 8 is an alternative embodiment of the enlarged portion of FIG. 6;

SUMMARY OF THE INVENTION

Figure 1:
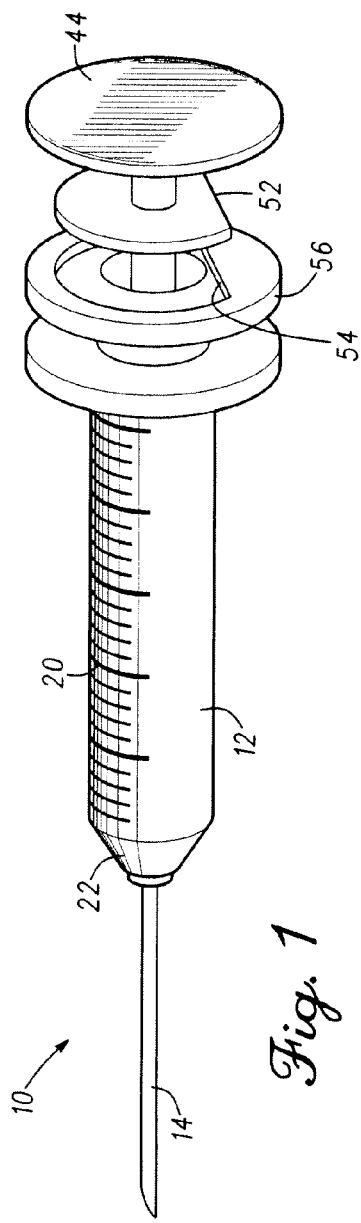
FIG. 1 is a perspective view of a safety syringe incorporating features of the present invention.
Figure 2:
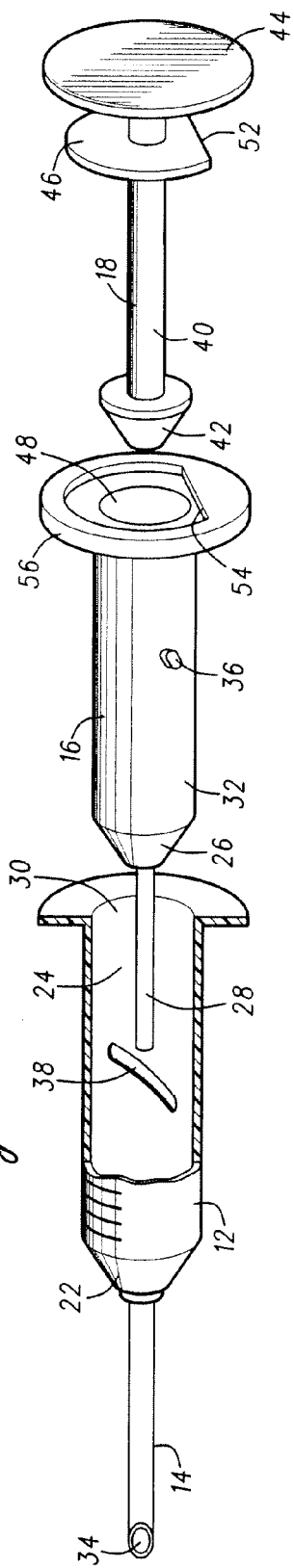
FIG. 2 is an exploded perspective view of the safety syringe of FIG. 1.

The present invention comprises a safety syringe adapted to inject substances into humans and animals. According to an embodiment of the present invention, the safety syringe has an outer casing that supports a conventional slant-cut hypodermic needle and an inner casing which supports a blunt cannula that is disposed inside the inner lumen of the hypodermic needle. The inner casing is keyed to the outer casing by one or more pins that engage helical tracks formed along the inner surface of the outer casing. Rotation of the inner casing relative to the outer casing advances the inner casing so that the blunt cannula is moved from a retracted position within the needle to an extended position in which the blunt end of the cannula extends beyond the tip of the needle. In operation, fluid intended for injection into the patient can be drawn into the inner casing in a manner similar to a conventional syringe by withdrawing the plunger, which is disposed within the inner casing. Because the needle is rigidly attached to the outer casing, the outer casing can be handled by skilled personnel as they would handle an ordinary hypodermic needle. The fluid contained within the inner casing is injected into the patient by depressing the plunger in a conventional manner. Once the plunger is fully depressed, the inner casing is rotated relative to the outer casing to advance the blunting cannula to its extended position thus blunting the tip of the needle. The inner casing may be manipulated directly or may be manipulated by means of keying the plunger to the inner casing so that twisting the plunger causes the inner casing to rotate. A shear pin or other frangible element between the plunger and inner casing may be provided to prevent the cannula from being retracted once it has been fully extended.

DETAILED DESCRIPTION

The drawing figures are intended to illustrate the general manner of construction and are not necessarily to scale. In the detailed description and in the drawing figures, specific illustrative examples are shown and herein described in detail. It should be understood, however, that the drawing figures and detailed description are not intended to limit the invention to the particular form disclosed, but are merely illustrative and intended to teach one of ordinary skill how to make and/or use the invention claimed herein and for setting forth the best mode for carrying out the invention.

With reference to the figures and in particular FIGS. 1-5, safety syringe 10 generally comprises a needle carrier 12, a hollow hypodermic needle 14, a syringe barrel 16 and a plunger 18. In the illustrative embodiment, needle carrier 12 is in the form of a hollow plastic cylinder formed of a high-strength plastic such as Polyamide (nylon), Polyphenylene Oxide (PPO), Acrylonitrile Butadiene Styrene (ABS) or Polyethylene (PE) having appropriate graduations 20 so that the amount of liquid in the safety syringe 10 can be determined. Needle carrier 12 has an end wall 22 to which hypodermic needle 14 is attached in a conventional manner. Central cavity 24 is generally cylindrical and is open at the end opposite end wall 22. In the illustrative embodiment, syringe barrel 16 is a hollow plastic cylinder also formed of a high-strength plastic such as nylon, PPO, ABS or PE having an end wall 26 to which a blunting cannula 28 is attached in a conventional manner.

Needle 14 is mounted coaxially with the central cavity 24 of needle carrier 12 and blunting cannula 28 is mounted coaxially to syringe barrel 16. The interior diameter 30 of central cavity 24 and the outer diameter 32 of syringe barrel 16 are sized to allow syringe barrel 16 to be inserted into needle carrier 12. Thus, when assembled, syringe barrel 16 is disposed within needle carrier 12 with blunting cannula 28 disposed within the central lumen 34 of needle 14. Syringe barrel 16 includes a pin or other track engaging member 36 which engages an angled slot, which is formed on the cylindrical surface defining central cavity 24 and therefore forms a helical track 38 formed in needle carrier 12. This couples needle carrier 12 to syringe barrel 16 in a manner the function of which will be explained more fully hereinafter.

Plunger 18 comprises a stem portion 40, a piston 42, a thumbpad 44 and a flange 46. The stem portion 40, thumbpad 44 and first engaging member or flange 46 of plunger 18 are preferably formed of a high-strength plastic such as nylon, PPO, ABS or PE. The interior cavity 48 of syringe barrel 16 has a substantially cylindrical cross section, an open proximal end and a distal end having a distal wall where the distal wall of syringe barrel 16 has an opening adapted to receive blunting cannula 28. The piston 42 is preferably formed of an elastomeric compound such as polyurethane, buna or silicone to enable it to sealingly engage the interior cavity 48 of syringe barrel 16. Flange 46 is generally circular in cross-section except for a flat 52 which engages a corresponding flat 54 formed in the second engaging member or collar 56 of syringe barrel 16 when plunger 18 is fully depressed.

With particular reference to FIGS. 3-5, safety syringe 10 is assembled by inserting syringe barrel 16 into needle carrier 12 until track engaging member 36 engages helical track 38. In the illustrative embodiment, both syringe barrel 16 and needle carrier 12 are formed of moderately flexible plastic material such as PE, which enables the mating parts to deform to allow track engaging member to snap in place within helical track 38 thus retaining syringe barrel 16 to needle carrier 12. With track engaging member 36 thus engaged in helical track 38, blunting cannula 28 is disposed within needle 14 with the distal end 58 of blunting cannula 28 recessed within the distal end 60 of needle 14.

To inject medication into the patient, plunger 18 is depressed in a conventional manner to expel the liquid from interior cavity 48 of syringe barrel 16 through the interior lumen 62 of blunting cannula 28 and through the central lumen 34 of needle 14. Once plunger 18 is fully depressed, the flat 52 of flange 46 engages the flat 54 formed in collar 56. This action keys plunger 18 to syringe barrel 16. Plunger 18 is then rotated through an appropriate arc, preferably between 45 degrees and 270 degrees and most preferably about 90 degrees. Syringe barrel 16 being keyed to plunger 18 moves through the same arc. Track engaging member 36 engaged in helical track 38 converts rotational motion of syringe barrel 16 into linear motion. The helical track 38 preferably has a helical pitch of between 30 degrees and 60 degrees. Accordingly, twisting plunger 18 advances syringe barrel 16 within needle carrier 12 until, as shown in FIG. 5, the blunt distal end 58 of blunting cannula 28 extends beyond the sharp distal end 60 of needle 14. This effectively blunts the distal end 60 of needle 14.

With reference to FIG. 6, helical track 38 formed in needle carrier 12 may include detent means 64 adapted to retain syringe barrel 16 in the position with blunting cannula 28 fully advanced. Detent means 64 may comprise a counterbore 64a adapted to receive track engaging member 36 as shown in FIG. 7. Alternatively, detent means 64 may comprise a plurality of lock members 64b as shown in FIG. 8.

Figure 9:
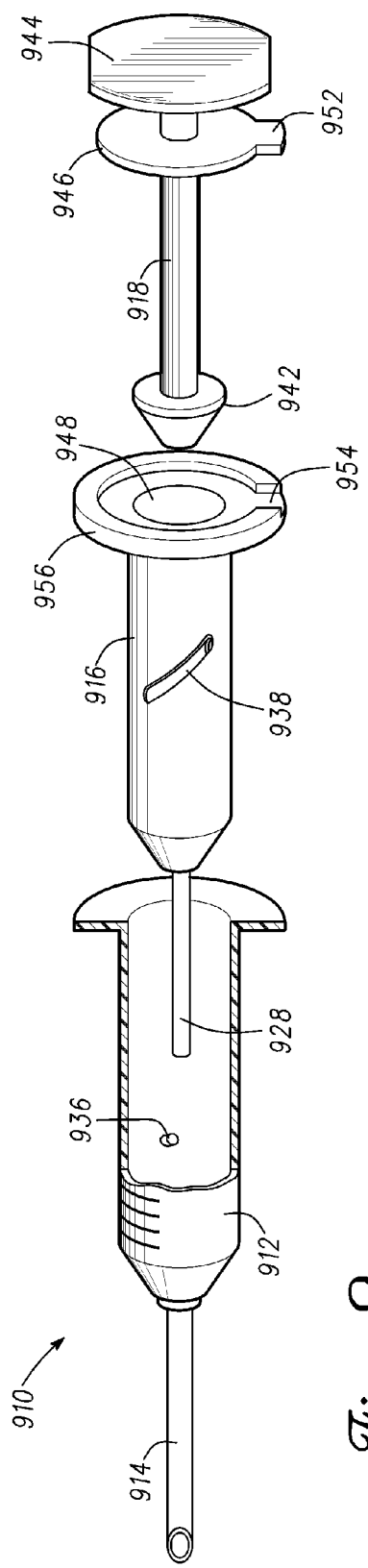
FIG. 9 is an exploded perspective view of an alternative embodiment of a safety syringe incorporating features of the present invention.

FIG. 9 shows an alternative embodiment of a safety syringe 910 comprising a needle carrier 912, hypodermic needle 914, syringe barrel 916 and plunger 918. In the illustrative embodiment of FIG. 9, needle carrier 912, includes a pin or other track engaging member 936 that engages a corresponding track 938 formed on the outer surface of syringe barrel 916. Plunger 918 includes a piston 942 that sealingly engages the interior cavity 948 of syringe barrel 916. Plunger 918 includes a thumbpad 944 and a first engaging member or flange 946. Flange 946 further includes a tab 952 that engages a corresponding recess 954 formed in second engaging member or collar 956 of syringe barrel 916. Tab 952 and recess 954 cooperate to key plunger 918 to syringe barrel 916 in a manner similar to the embodiment of FIGS. 1-5, however, tab 952 may be designed to fail by breaking off at a predetermined torque such that once blunting cannula 928 has been moved to its fully extended position, tab 952 breaks off rendering it difficult or impossible to retract blunting cannula 928 from its fully extended position.

Figure 10:
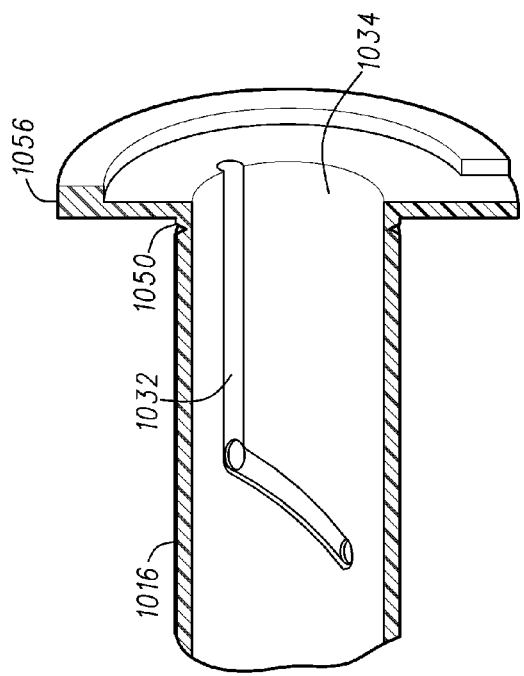
FIG. 10 is a partial cutaway view of an alternative embodiment of a syringe barrel incorporating features of the present invention.

Although certain illustrative embodiments and methods have been disclosed herein, it will be apparent from the foregoing disclosure to those skilled in the art that variations and modifications of such embodiments and methods may be made without departing from the invention. For example, although in the illustrative embodiment of FIGS. 1-9, the syringe barrel and needle carrier are formed of plastic materials capable of deforming to allow the safety syringe to be assembled, a track 1032 may be provided that extends to the open end 1034 of syringe barrel 1016. Additionally, although in the illustrative embodiment of FIG. 9, tab 952 comprised a frangible element as shown in the illustrative embodiment of FIG. 10, second engaging member or collar 1056 of syringe barrel 1016 may include a frangible portion, such as an undercut portion 1050 designed to break off rendering it difficult or impossible to retract the blunting cannula once fully extended. Finally, although track 38 is shown as a recessed portion in the embodiment of FIGS. 6-10, for ease of manufacturing, track 38 may comprise a slot that extends through the exterior wall of needle carrier 12. Accordingly, it is intended that the invention should be limited only to the extent required by the appended claims and the rules and principles of applicable law. Additionally, as used herein, unless otherwise specifically defined, the terms "substantially" or "generally" when used with mathematical concepts or measurements mean within ±10 degrees of angle or within 10 percent of the measurement, whichever is greater.

What is claimed is:

1. A safety syringe comprising:
a needle carrier, said needle carrier comprising a body having a central cavity, the central cavity of said needle carrier having a substantially cylindrical cross section, an open end and an end wall, the end wall of said needle carrier having an opening adapted to receive a hollow needle;
a hollow needle attached to the end wall of said needle carrier, said hollow needle having a sharp distal end and a central lumen opening into the central cavity of said needle carrier
a syringe barrel comprising a generally cylindrical body disposed within the central cavity of said needle carrier, said syringe barrel having a proximal end, a distal end and an interior cavity, the interior cavity of said syringe barrel having a substantially cylindrical cross section, an open proximal end and a distal end having a distal wall, the distal wall of said syringe barrel having an opening adapted to receive a cannula;
a cannula attached to the distal end of said syringe barrel and disposed coaxially within the central lumen of said hollow needle, said cannula having an interior lumen opening into the interior cavity of said syringe barrel, said cannula having a blunt distal end, said syringe barrel being moveable between a retracted position in which the blunt end of said cannula is within the central lumen of said hollow needle to an extended position in which the blunt end of said cannula extends beyond the sharp distal end of said needle; and
a helical track and track engaging member assembly coupling said syringe barrel and said needle carrier for advancing said syringe barrel, whereby rotating said syringe barrel relative to said needle carrier advances said syringe barrel and said cannula from the retracted position to the extended position.

2. The safety syringe of claim 1, further comprising:
a syringe plunger, said syringe plunger comprising a piston moveable from a withdrawn position to a depressed position for expelling a liquid from said syringe barrel, said syringe plunger further comprising a first engaging member, said first engaging member adapted to engage a corresponding second engaging member formed on said syringe barrel for transmitting rotation between said syringe plunger and said syringe barrel, said first engaging member being disengaged from said second engaging member in the withdrawn position and being engaged with said second engaging member in the depressed position.

3. The safety syringe of claim 2, wherein:
said first engaging member comprises a flange having a noncircular feature and said second engaging member comprises a corresponding feature formed on said syringe barrel.

4. The safety syringe of claim 2, wherein:
one of said first and second engaging members comprises a frangible element that breaks at a predetermined torque to prevent subsequent rotation of said syringe plunger from retracting said cannula.

5. The safety syringe of claim 4, wherein:
said frangible element comprises a tab formed on said first engaging member.

6. The safety syringe of claim 4, wherein:
said frangible element comprises a frangible portion formed on said syringe barrel.

7. The safety syringe of claim 1, wherein:
said helical track and track engaging member assembly comprises a pin formed on said syringe barrel and a slot formed in said needle carrier.

8. The safety syringe of claim 1, wherein:
said helical track and track engaging member assembly comprises a pin formed on said needle carrier and a slot formed in said syringe barrel.

9. The safety syringe of claim 1, further comprising:
detents for retaining said syringe barrel in a fixed rotational position relative to the needle carrier with the cannula in the extended position.

10. The safety syringe of claim 1, wherein:
said helical track and track engaging member assembly comprises a helical track having a helical pitch of between 30 degrees and 60 degrees.

11. The safety syringe of claim 1, wherein:
said helical track and track engaging member assembly comprises a helical track that extends along a helical path of no more than 270 degrees of arc.

12. A safety syringe comprising:
a needle carrier, said needle carrier comprising a body having a central cavity, the central cavity of said needle carrier having a substantially cylindrical cross section, an open end and an end wall, the distal wall of said needle carrier having an opening adapted to receive a hollow needle;
a hollow needle attached to the end wall of said needle carrier, said hollow needle having a sharp distal end and a central lumen opening into the central cavity of said needle carrier;
a syringe barrel comprising a generally cylindrical body disposed within the central cavity of said needle carrier, said syringe barrel having a proximal end, a distal end and an interior cavity, the interior cavity of said syringe barrel having a substantially cylindrical cross section, an open proximal end and a distal end having a distal wall, the distal wall of said syringe barrel having an opening adapted to receive a cannula;
a cannula attached to the distal end of said syringe barrel and disposed coaxially within the central lumen of said hollow needle, said cannula having an interior lumen opening into the interior cavity of said syringe barrel, said cannula having a blunt distal end, said syringe barrel being moveable between a retracted position in which the blunt end of said cannula is within the central lumen of said hollow needle to an extended position in which the blunt end of said cannula extends beyond the sharp distal end of said needle;
an angled track and track engaging member assembly coupling said syringe barrel and said needle carrier for advancing said syringe barrel, whereby rotating said syringe barrel relative to said needle carrier advances said syringe barrel and said cannula from the retracted position to the extended position; and
a syringe plunger, said syringe plunger comprising a piston moveable from a withdrawn position to a depressed position for expelling a liquid from said syringe barrel, said syringe plunger further comprising a non-circular feature adapted to engage a corresponding non-circular feature formed on said syringe barrel for transmitting rotation between said syringe plunger and said syringe barrel when said syringe plunger is in the depressed position;
whereby said cannula is advanced from the retracted position to the extended position by depressing said syringe plunger from the withdrawn position to the depressed position to engage the non-circular feature of said syringe plunger with the corresponding non-circular feature formed on said syringe barrel then twisting said syringe plunger relative to said needle carrier.

13. The safety syringe of claim 12, wherein:
one of said syringe plunger and said syringe barrel comprises a frangible element that breaks at a predetermined torque to prevent subsequent rotation of said syringe plunger from retracting said cannula.

14. The safety syringe of claim 12, wherein:
said angled track and track engaging member assembly comprises a pin formed on said syringe barrel and a slot formed in said needle carrier.

15. The safety syringe of claim 12, wherein:
said angled track and track engaging member assembly comprises a pin formed on said needle carrier and a slot formed in said syringe barrel.

\* \* \* \* \*